(12) United States Patent
Simionescu et al.

(10) Patent No.: US 6,214,055 B1
(45) Date of Patent: Apr. 10, 2001

(54) METHOD AND KIT FOR RAPID PREPARATION OF AUTOLOGOUS TISSUE MEDICAL DEVICES

(75) Inventors: Dan Simionescu; Agneta Simionescu, both of Targu Mures (RO)

(73) Assignee: Mures Cardiovascular Research, Inc., Saint Paul, MN (US)

( * ) Notice: Subject to any disclaimer, the term of this patent is extended or adjusted under 35 U.S.C. 154(b) by 0 days.

(21) Appl. No.: 09/183,426

(22) Filed: Oct. 30, 1998

(51) Int. Cl.$^7$ ........................................... A61F 2/00
(52) U.S. Cl. ........................................ 623/23.72; 623/2.42
(58) Field of Search ....................... 623/915–918, 623/1.47, 1.48, 2.13–2.16, 2.42, 920–922, 23.72

(56) References Cited

U.S. PATENT DOCUMENTS

| | | | |
|---|---|---|---|
| 3,988,782 | * | 11/1976 | Dardik et al. . |
| 4,120,649 | * | 10/1978 | Schechter . |
| 4,553,974 | * | 11/1985 | Dewanjee . |
| 4,582,640 | * | 4/1986 | Smestad et al. . |
| 4,755,593 | * | 7/1988 | Lauren . |
| 4,786,287 | * | 11/1988 | Nashef et al. . |
| 5,188,834 | * | 2/1993 | Grimm et al. ..................... 424/422 |
| 5,336,616 | * | 8/1994 | Livesey et al. ................. 435/240.2 |
| 5,344,442 | | 9/1994 | Deac ...................................... 623/2 |
| 5,500,015 | | 3/1996 | Deac ...................................... 623/2 |
| 5,697,972 | | 12/1997 | Kim et al. ............................. 623/2 |
| 5,879,383 | * | 3/1999 | Bruchman et al. .................. 623/1 |

OTHER PUBLICATIONS

Golomb PhD, Gershon, et al., The Role of Glutarldehyde–Induced Cross–links in Calcification of Bovine Pericardium Used in Cardiac Valve Bioprostheses, pp. 122–130.

Nimni, M. E., et al., Chemically modified collagen: A natural biomaterial for tissue replacement, pp. 741–771.

Nimni, Marcel E., A Defect in the Intramolecular and Intermolecular Cross–linking of Collagen Caused by Penicillamine, pp. 1457–1466.

Ross, Donald N., et al., The Annals of Thoracic Surgery, A Two–Year Experience with Supported Autologous Fascia Lata for Heart Valve Replacement, vol. 13, No. 2, Feb. 1972, pp. 97–103.

Schoen M.D., Frederick J., Pathological Considerations in Replacement Cardiac Valves, vol. 1, No. 1, Jan.–Mar. 1992:29–52.

* cited by examiner

Primary Examiner—Michael J. Milano
(74) Attorney, Agent, or Firm—Kinney & Lange, P.A.

(57) ABSTRACT

A method for the rapid chemical treatment of autologous connective tissues which enhances biocompatibility by reducing cytotoxicity, immunogenicity and calcification without impairing the mechanical properties of the fixed tissue. The procedure includes a short exposure of the autologous biological tissue to a dialdehyde fixative followed by the rapid neutralization of excess aldehyde with an aminoacid solution.

16 Claims, 1 Drawing Sheet

METHOD AND KIT FOR RAPID PREPARATION OF AUTOLOGOUS TISSUE MEDICAL DEVICES

CROSS-REFERENCE TO RELATED APPLICATIONS

None.

BACKGROUND OF THE INVENTION

The present invention relates generally to implantable biomaterials prepared by a rapid technique from aldehyde-treated autologous connective tissues, and particularly to such medical devices as tissue heart valves, patches, conduits and other intravascular or intracardiac prosthetic devices which possess improved biocompatibility and anti-calcification properties.

Biomaterials prepared from glutaraldehyde crosslinked heterologous connective tissues such as bovine pericardium or porcine aortic valves are widely used in reconstructive and replacement procedures such as cardiovascular surgery in the form of bioprosthetic heart valves, valved or non-valved conduits, fashionable patches and the like. Stabilization of tissues with glutaraldehyde improves their biomechanical properties, increases their resistance to collagenase and reduces tissue-induced thrombogenicity. See Nimni et al., *J. Biol. Chem.*, 243:1457–1466 (1968). The alternative of using native, non-crosslinked tissues is disfavored because performance is limited due to tissue thickening and shrinkage, enzymatic digestion and subsequent loss of mechanical properties. See Ross et al., *Ann. Thorac. Surg.*, 13:97–103 (1972). These reactions are characteristic of a tissue which is exposed to a new, non-physiological environment (such as pericardium exposed to flowing blood and extreme mechanical stress). Treatment of biological tissues with glutaraldehyde prevents these phenomenon by stopping cell metabolism and thus rendering the biomaterial usable in the new environment.

Glutaraldehyde, $C_5H_8O_2$, contains two aldehyde groups and is commonly used in the fixation of biological tissues. Glutaraldehyde is a water soluble, reactive dialdehyde which when brought in contact with biological tissues penetrates fibrous connective tissues at a slow rate and interacts with terminal amino groups exposed by the tissue components. Several studies have shown that optimal crosslinking occurs after 5 or more days in the glutaraldehyde solution, while a short exposure (10–15 minutes) penetrates tissues only on their surface leaving a central core of suboptimally fixed structures. See Nimni et al., *J. Biomed. Mater. Res.*, 21:741–771 (1987). The chemistry of glutaraldehyde crosslinking involves three main aspects of interest to this invention: (1) by means of the two reactive aldehyde groups, glutaraldehyde is capable of creating intra and intermolecular crosslinks, provided that the exposed amino groups are optimally spaced; (2) the second product of this reaction is glutaraldehyde which has reacted with only one amino group, thus exposing a free aldehyde moiety (unipoint fixation); and (3) glutaraldehyde polymerizes in time at neutral pH giving rise to polymers which are unstable and with time can release significant amounts of cytotoxic glutaraldehyde molecules into solution.

It is generally accepted that biomaterials prepared from tissues treated with glutaraldehyde for at least 14 days provide surgeons with biocompatible implantable medical devices with good long term durability. Still, several limitations of current devices indicate the need for improved biomaterials. See Schoen et al., *Cardiovasc. Pathol.*, 1:29–52 (1992); Golomb G. et al., *Am. J Pathol.*, 127:122–130 (1987).

The major limitation of current devices is calcification, the process in which organic tissue becomes hardened by the deposition of lime salts in the tissues. Calcification is the main limiting factor that affects the long term durability of glutaraldehyde treated tissues due to an interplay of a multitude of host factors (age, renal failure, hyperparathyroidism, mechanical stress) and implant related elements (glutaraldehyde per se, calcium binding matrix components, cellularity). The degree of calcium deposition is proportional to the degree of glutaraldehyde incorporation. It is thus believed that suoptimal fixation attained by a short term exposure to glutaraldehyde can induce less calcification, while maintaining the required mechanical characteristics.

Another limitation of current devices is variability. Variability in the clinical outcome has been attributed to the inherent variability in animal characteristics and tissue collection criteria such as age, race, nutritional state, sex, tissue quality, handling, cleaning, storage and transportation. Proper tissue selection requires consideration of a multitude of aspects such as collagen content, vascularity, cellularity, thickness and mechanical properties.

A third limitation of current devices is immunogenicity, the capacity to stimulate the formation of antibodies in a particular biological system. Although glutaraldehyde reduces considerably tissue antigenicity, a low-level of humoral (antibodies to collagen) and cellular (moderate leukocyte infiltration) immune response has been identified in animal and human subjects bearing these devices. Moreover, several studies have established a correlation between immune reactions and calcification.

Another limitation of current devices is viability, the ability to live, grow, and develop in the new biological system. Long term glutaraldehyde fixation protocols render tissues non-viable and prone to calcification—cells within the tissue are exposed to hypoxia (due to the delay between harvest and fixation) and after exposure the glutaraldehyde, devitalized cells are prone to calcification. Longer delays before completing fixation correlates with more pronounced calcification.

A fifth limitation of current devices is endothelialization in which free aldehyde groups derived from unipoint fixation and exposed towards the tissue surface inhibit endothelial cell coverage by the host.

Another limitation of current devices is cytotoxicity. Glutaraldehyde molecules may leach out, induce a local pro-inflammatory reaction and reduce tissue integration into the host organ. Simple repetitive washing in saline is ineffective in reducing cytotoxicity and pro-inflammatory reactions.

Another limitation of current devices is sterilization, the process of completely removing or destroying all microorganisms on a substance. The long procedure required for manufacturing of bioprosthetic tissues demands both careful bacteriological monitoring of each step and implementation of a final sterilization/storage step which may affect mechanical properties of the final product.

The present invention overcomes some of the above-mentioned limitations, without compromising the advantages gained by glutaraldehyde fixation. The major advantages of the proposed rapid glutaraldehyde fixation include: (1) the use of carefully selected autologous tissue will minimize variability and reduce the immunologic response; (2) the immediate fixation of autologous tissues will reduce the unwanted delay between tissue harvest and fixation, will warrant sterility and reduce the tendency to calcification, will limit glutaraldehyde polymerization and increase the possibility of saving a certain proportion of live cells, especially in the supoptimal fixed central areas; and (3) the development of a rapid glutaraldehyde neutralization procedure will ensure full depletion of deleterious aldehyde groups and leachable glutaraldehyde molecules thus providing with a non-cytotoxic and possibly endothelium-friendly biomaterial.

BRIEF SUMMARY OF THE INVENTION

The present invention provides a rapid glutaraldehyde fixation and neutralization procedure which comprises three main steps: (1) autologous tissue harvesting and preparation for fixation; (2) short fixation in standardized glutaraldehyde solution; and (3) a rapid protocol for washing and neutralization of glutaraldehyde. In a preferred embodiment, the sterile fixation solution is composed of purified glutaraldehyde, buffered with a non-phosphate compound and supplemented with cations which compete for tissue calcium binding sites. The purified glutaraldehyde is preferably monitored for purity and the buffer is at pH 7.4 in stabilized bicarbonate, borate or N-2-hydroxyethylpiperazine N-ethanesulfonic acid and the like supplemented with magnesium ions. A preferred neutralization solution is comprised of unbranched, physiological alpha amino acids, in particular glycine, in the same buffer.

The treatment of the present invention is amenable to implementation in the operating room, especially for intraoperative reconstruction or replacement of cardiac and cardiovascular tissues such as cardiac valves, interventricular septum, blood vessels from autologous tissues such as pericardium, cardiac valves, arterial and venous walls, fascia lata and the like. The present invention is also adequate for preparing autologous tissues for use in other types of reconstructive surgery such as maxillofacial, orthopaedic and the like. By comparison with the long-term heterologous tissues, autologous biomaterials treated with this procedure are characterized by reduced immunogenicity, cytotoxicity and calcification without impairing the mechanical durability and strength of the fixed tissue.

BRIEF DESCRIPTION OF THE DRAWINGS

The present invention will be further explained with reference to the attached figures, wherein like structures are referred to by like numerals throughout the several views.

Figure 1:
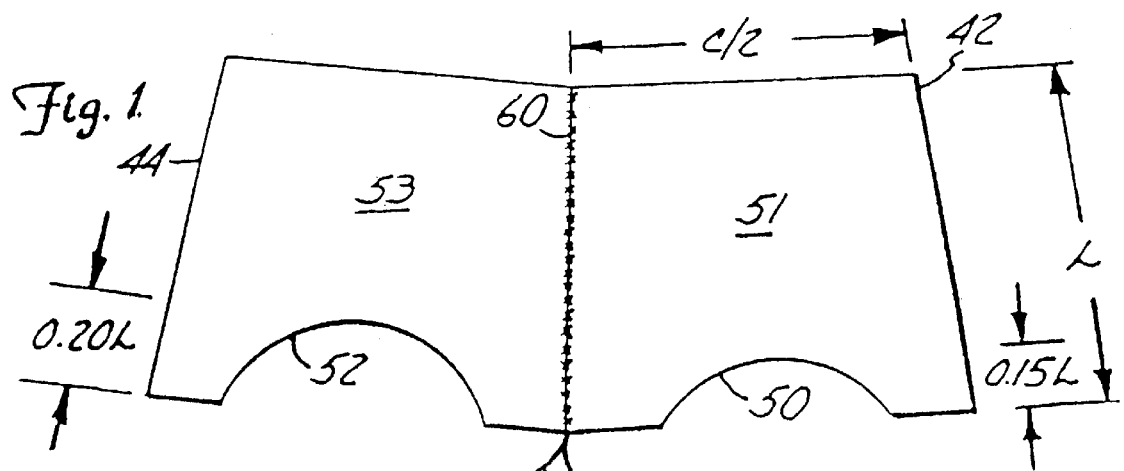
FIG. 1 is a plan view of trapezoidal membranes for construction of a mitral valve in accordance with the present invention.

While the above-identified drawings set forth preferred embodiments of the present invention, other embodiments of the present invention are also contemplated, as noted in the discussion. This disclosure presents illustrative embodiments of the present invention by way of representation and not limitation. Numerous other modifications and embodiments can be devised by those skilled in the art which fall within the scope and spirit of the principles of this invention.

DETAILED DESCRIPTION

The present invention provides a rapid fixation procedure by which autologous tissues are chemically modified in such a way as to yield medical devices which are implantable in humans or animals.

Definitions

"Autologous tissue" is any tissue harvested from the human or animal subject such as heart valves, pericardium, arteries, veins, organ capsules, arterial and venous walls, fascia lata, tendons, skin, trachea, medical devices that incorporate rapidly fixed and neutralized tissue, and the like, which is intended to be reimplanted in the same subject. "Procedure" relates to any manipulations or chemical treatments that the tissues are subjected to in order to prepare the tissue. Specifically, "procedure" relates to tissue selection, washes, cleaning and removal of unwanted segments, aldehyde stabilization, washing and neutralization. "Fixation" or "stabilization" involves the exposure of tissue to crosslinking reagents such as monoaldehyes, dialdehydes, polyaldehydes or any other reagents or combination of agents which introduce in the tissue a considerable number of chemical covalent crosslinks thus stabilizing the tissue protein matrix. "Neutralization" relates to any chemical or physical procedure that aims at quenching or cancellation of the toxic effects that could be induced by certain chemical groups or molecules. "Rapid" designates the shortest, most practical and reasonable period of time during which the autologous tissue is harvested, treatment is applied and the final product is ready to be implanted. For example, in the case of reconstruction of a diseased mitral valve with autologous pericardium stabilized by means of the present invention, the time allocated from tissue harvest to actual surgical implantation should not exceed 30–40 minutes. "Implantable" means any application in which the device is intended to be implanted in a human or animal body while "medical device" means any structure or mechanism intended for use in the cure, mitigation or prevention of a disease. Examples encompassed by this invention include reconstruction or replacement of heart valves, blood vessels and other diseased connective tissues or organs.

General Methodology

The present invention comprises three main steps: (1) autologous tissue harvesting and preparation for fixation; (2) short fixation in standardized glutaraldehyde solution; and (3) a rapid protocol for washing and neutralization of glutaraldehyde.

The first step is harvesting of the autologous tissue from the site of choice. A preferred method of harvesting autologous tissue is known in the art and described in U.S. Pat. Nos. 5,344,442 and 5,500,015 to Radu Deac, which are incorporated herein by reference and assigned to the same assignee as the present application. The quality, thickness, orientation of fibers and strength may determine the outcome of the medical device. Thus, specifically in the case of pericardium, mapping of these characteristics facilitate proper tissue selection. Detailed mapping of mechanical and biological characteristics of whole pericardia has revealed that the areas overlying the anterior ventricular surface were designated as "areas of choice" for tissue selection.

The second step involves a short fixation in standardized glutaraldehyde solution. The sterile fixation solution is composed of purified glutaraldehyde, buffered with a non-phosphate compound and supplemented with cations which compete for tissue calcium binding sites. The purified glutaraldehyde is prepared as a 0.2 to 0.7% solution, preferably monitored for the presence of polymers at 235 nm and of monomers at 280 nm, by a UV spectrophotometer, in particular observing that the ratio of absorbance at 280 nm/235 nm exceeds 2.5. Removal of material which absorbs at 235 nm is necessary because glutaraldehyde polymers are non-crosslinking and very cytotoxic. Purification can be achieved by various techniques, including absorption, vacuum distillation. Some producers supply pure glutaraldehyde.

The buffer is preferably pH 7.4 stabilized bicarbonate, borate or N-2-hydroxyethlpiperazine N-ethanesulfonic acid or the like supplemented with magnesium ions. The choice of buffer requires consideration of the following factors: (1) it has to be compatible with glutaraldehyde, i.e., should not contain free amino groups that might react with aldehyde groups (e.g., Tris buffers); (2) it should provide good buffering capabilities at around pH 7.4; and (3) it is suggested that non-phosphate buffer compounds are used. The use of non-phosphate buffers is still a matter of controversy because some investigators have shown that tissue fixation in phosphate buffered glutaraldehyde promotes mineralization in experimental models, while others have contradicted these results. In the present invention, non-phosphate buffered glutaraldehyde gave excellent results in experimental and clinical studies. Supplementation of the fixation solution with cations which compete for tissue calcium binding sites such as magnesium, aluminum, ferric and others can reduce the tendency to calcification. The choice of the cation is largely dependent on the tissue structure and the site of implantation. In particular, pericardium fixed in the presence of magnesium ions accumulated less calcium in experimental calcification studies. After preparation, the fixation solution is sterilized by filtration through 0.22 u filters dispensed in sterile vials and stored at 4° C. The fixation step will be carried out at room temperature, by placing the autologous tissue directly in the vial and can be timed between 8 to 15 minutes. A 5 to 10 minute wash in physiological saline will remove some of the unbound glutaraldehyde molecules.

The final neutralization step is a prerequisite for preparing aldehyde treated tissues for human or animal implantation. Many water soluble, non toxic amino-containing compounds may be used for neutralization. The preferred embodiment of the present invention uses unbranched alpha amino acids, such as glycine. The aminoacids are dissolved at a concentration of 0.05 to 0.4 M in the same buffer used for glutaraldehyde preparation, sterilized by filtration, dispensed in sterile vials and stored at 4° C. The neutralization step is carried out at room temperature, by transferring the saline washed, glutaraldehyde fixed autologous tissue directly in the aminoacid solution and can be timed between 8 to 15 minutes. The neutralization step is repeated once, and is followed by two to three final 5 to 10 minute washes in physiological saline to remove the unbound compounds. The tissue is then ready for implantation. The entire procedure requires between 25 to 40 minutes.

As shown in FIG. 1, scallops 50 and 52 are of equal width and unequal depth so that leaflets 51 and 53 (formed between each scallop and the respective rim) are of unequal size. The larger of the two leaflets (smaller scallop) is anterior leaflet 51 for the valve, and the smaller of the two leaflets (larger scallop) is the smaller posterior leaflet 53. Each leaflet 51 and 53 has a trapezoidal shape with the top of the trapezoid being equal to C/2, where C is the circumference of the mitral ring. The height of each leaflet forms the length L of the valve and is equal to C/2. The long base of each leaflet is equal to 0.6 C, or about 1.2 times the length of the short base. The scallop is centered on the base and has a width of 0.4 C, leaving apical zones for each leaflet equal to 0.1 C. It will be appreciated that upon joining leaflets, the apical zones attached to the papillary muscles by the chordae tendineae will have a width of about 0.2 C.

The depths of scallops 50 and 52 are chosen to assure proper operation of the valve; the depths being deep enough as to provide good opening and flow characteristics, but not so deep as to exhibit poor closing characteristics. A depth of 15% of the height (0.15 L) of the leaflet for the anterior leaflet and 20% of the height (0.20 L) of the leaflet for the posterior leaflet provide good operating characteristics for the resulting valve. If the valve is manufactured in a central laboratory, the valve is tested for optimum operating characteristics (flow, opening and closing) before being supplied to the surgeon. If the valve and scallop profile are to be finished by the surgeon, the surgeon will cut openings at the positions where the scallops will be formed, and the valve is tested for opening, flow and closing characteristics. The tests are repeated with deeper openings until optimum operating characteristics are achieved. The elliptical scallops 50 and 52 are cut into the membranes to the depths of the openings, thereby forming the finished valve. Conveniently, the surgeon is provided with cutting dies according to the present invention to form the scallops.

Membranes 42 and 44 are joined together with double continuous 2–0 (Goretex) sutures 60 with the inferior end of each suture buttressed between two small pledgets of Teflon. The free ends 62 of the sutures are left uncut for attachment to the papillary muscles.

Under cardiopulmonary bypass conditions, the left atrium is opened and the diseased mitral valve excised, leaving a few millimeters of chordae tendineae above each papillary muscle. The circumference, C, of the mitral ring is measured (such as with an oval obturator), and the distance, D, is measured between the tip of the papillary muscle (at the point of insertion of the main chordae) and the mitral ring (at the point nearest the papillary muscle). The valve size is selected so that the circumference of the artificial valve equals the measured circumference, C, of the mitral ring, and the length L of the valve equals C/2. As a check on the length L of the valve, the surgeon will calculate the equivalent diameter, d, of the mitral ring from the circumference, C, and check that L approximately equals 115% of the measured distance between the mitral ring and the papillary muscle plus d/2. Thus, L≈1.15(D+d/2).

Normally, the lengths of the flaps are equal. In rare cases the distance between the mitral ring and the each papillary muscle is different, in which case the surgeon will adjust the length of the flaps in accordance with the relationship L=1.15(D+d/2).

The left ventricle continues to change in size throughout most of life. Consequently, it is important that any artificial valve compensate for change in size of the left ventricle, or re-operation will be required. The above relationship provide adequate dimensions for the artificial valve to reduce the likelihood of re-operation.

In the case of a replacement valve formed during the operation from autologous pericardium, cutting dies are chosen in accordance with the foregoing relationships for the calculated sizes of the graft and the inferior margins of the selected membranes are trimmed to a desired elliptical shape as shown. The lateral edges of the membranes are sutured together with double continuous 2/0 (Goretex) sutures.

Figure 2:
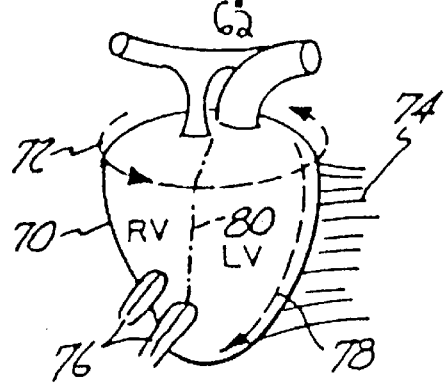
FIG. 2 is a view of a bovine pericardium which is mapped in accordance with the present invention for selecting and forming the trapezoidal membranes employed in the valve.
Figure 3:
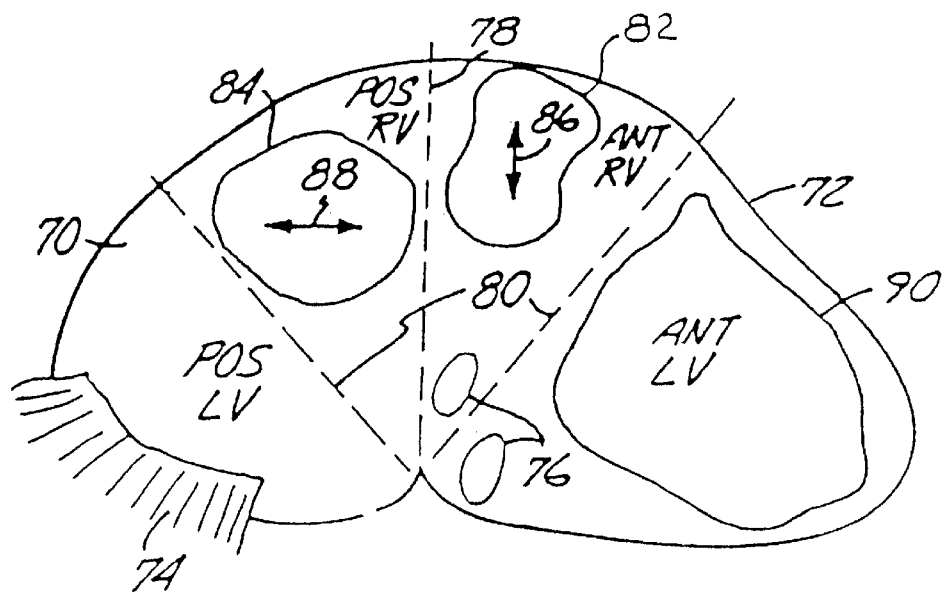
FIG. 3 is an enlarged view of a bovine pericardium which is mapped in accordance with the present invention for selecting and forming the trapezoidal membranes employed in the valve.

FIGS. 2 and 3 illustrate the technique for harvesting pericardium for construction of the leaflets illustrated in FIG. 1. The technique for harvesting pericardium will be described in connection with bovine pericardium, but it is understood that the techniques described herein are equally applicable to other animal and human pericardium, including donor pericardium. FIG. 2 illustrates the pericardium sac 70 surrounding the heart with dotted line 72 representing the base of the pericardium. The aorta, pulmonary arteries, pulmonary veins and other major veins and arteries are illustrated as emanating from the base of the pericardium. Muscle fiber 74 attaches the pericardium to the diaphragm adjacent the posterior side of the left ventricle. The anterior side of the pericardium is attached to the sternum by two sterno-periocardic ligaments 76. The pericardium sac is shown divided into four regions, the anterior and posterior regions being separated by dotted line 78 and the left and right ventricles being separated by dotted line 80. FIG. 3 shows the pericardium sac 70 laid out flat as if it had been cut along base line 72 and part of line 78. The right side of FIG. 3 illustrates the region of the anterior side of the left ventricle, and the left side of FIG. 3 illustrates the posterior side of the left ventricle.

Experimentation conducted on bovine pericardium revealed two areas 82 and 84 over the anterior and posterior regions of the right ventricle which exhibit superior tearing strengths, unidirectional fiber orientation and greater thicknesses than other regions of the pericardium. Regions 82 and 84 of bovine pericardium taken from twenty-two week old calves, exhibited thicknesses between about 0.45 and 0.65 millimeters, with the fibrous tissue being orientated predominantly in a direction indicated by arrow 86 in region 82, and in the direction of arrow 88 in region 84. The material in the regions 82 and 84 was found to exhibit the greatest resistance to tearing in directions indicated by the arrows 86 and 88. Another region, 90, predominantly overlying the anterior region of the left ventricle, was found also to be of significantly thick pericardium, but fiber orientation tended to be more mixed. Suture holding power for the regions 82, 84 and 90 were found to be higher than other regions, usually in the range between about 40 and 60 megapascals (MPa).

Where pericardium is used for construction of a mitral valve according to the present invention, it is preferred that the pericardium be harvested from the regions 82 and/or 84. Although bovine pericardium is specifically described, it is believed human pericardium exhibits similar characteristics and that the preferred region of harvest is the regions 82 and 84 adjacent the right ventricle. Hence, donor pericardium may be employed in constructing the valve.

The valve may be constructed by excising pericardium from the regions 82 and 84, selecting cutting dies for cutting the pericardium in accordance with the sizes described above, orienting the cutting dies so that the fibrous orientation of the pericardium is orientated generally along the dimension L in FIG. 1 (between the rim of the intended mitral valve and the apical ends to be attached to the papillary muscles), and cutting the pericardium into the individual trapezoidal shape, with elliptical scallops, as previously described. The trapezoidal membranes are sutured along their edges to form the mitral valve.

The treatment is amenable to implementation in the operating room, especially for intraoperative reconstruction or replacement of cardiac and cardiovascular tissues such as cardiac valves, interventricular septum, blood vessels, etc. As such, a kit may be provided containing a plurality of pairs of cutting dies each having cutting edges arranged to sever pericardium into the sizes and shapes of membranes 42 and 44 in FIG. 1, and the materials required for treatment of the present invention (i.e., solutions, buffers and the like) for harvesting autologous tissue. Hence, each die of each pair has a generally trapezoidal shape with a short base length selected by the surgeon equal to one-half the measured circumference of the mitral ring. The length L, along one edge of the membrane is equal to the length of the short base, the long base is equal to 1.2 times the length of the short base, and the elliptical scallop has a width equal to 0.8 times the short base and is centered on the long base. The depth of the scallop for one die of each pair is 0.15 times the length, whereas the depth of the scallop for the other die of each pair is 0.20 times the length. Each pair of dies is selected for a different nominal circumference of the mitral ring.

By comparison with the long-term fixed heterologous tissues such as bovine pericardium, autologous biomaterials treated with this procedure are characterized by reduced immunogenicity, cytotoxicity and calcification without impairing the mechanical durability and strength of the fixed tissue.

EXAMPLES

The present invention is more particularly described in the following examples which are intended as illustrations only since numerous modifications and variations within the scope of the present invention will be apparent to those skilled in the art.

Pericardial tissue was prepared with the rapid fixation protocol described above and the degree of aldehyde neutralization was assessed in vitro by quantifying free aldehyde groups. Furthermore, reduction of the glutaraldehyde cytotoxicity was investigated in a three-dimensional collagen gel system using living cells. Tissue prepared according to this invention, referred to in the following examples as "neutralized", was compared to pericardial tissue prepared with long term fixation techniques (designated as "control"). The two groups were subjected to mechanical tests and analyzed for resistance to enzymatic digestion, crosslink stability, calcification and biocompatibility. The neutralized group was prepared by fixing fresh bovine pericardial tissue for 10 minutes in 0.7% buffered glutaraldehyde in a ratio of 100 ml to 1 g wet tissue. After a 5 minute wash in saline (step 1), neutralization was carried out by incubating the tissue for 5 minutes in a 0.2 M buffered glycine solution (step 2). The tissue was transferred to a fresh vial of glycine and incubated for another 5 minutes (step 3) followed by a final 10 minute wash in saline (step 4). The control group consisted of fresh bovine pericardial tissue fixed for 14 days in 0.7% buffered glutarldehyde. The tissues were then subjected to three separate washes in fresh saline for 5 minutes each (steps 1–3) followed by a final wash in fresh saline for 10 minutes (step 4).

Example 1—Neutralization

Samples from both groups were incubated in sterile saline at 37° C. for 4 weeks for assessment of crosslink stability (step 5). At the end of the experiment, tissue was dried and total dry weight was calculated. Solutions from each incubation step were saved and aldehyde groups were assayed with a 2, 4 dinitrophenylhydrazine method using a standard curve of glutaraldehyde. The results are tabulated in Table 1. Sensitivity of the technique is 1 ug glutaraldehyde per ml.

TABLE 1

Glutaraldehyde Content in Wash Solutions (ug/ml, ±SD, n = 8)

| Step | Control Group | Neutralized Group |
|---|---|---|
| 1. Saline wash | 119 ± 9 | 123 ± 8 |
| 2. Saline wash (control group) OR glycine incubate (neutralized group) | 68 ± 7 | 23 ± 4 |
| 3. Saline wash (control group) OR Glycine incubate (neutralized group) | 46 ± 5 | 8 ± 2 |
| 4. Saline wash | 42 ± 5 | 3 ± 0.5 |
| 5. Saline incubate | 126 ± 3 | 2 ± 0.3 |

Consecutive washes in saline (control group) did not provide with proper removal of residual glutaraldehyde even after 4 washes. Moreover, significant amounts of glutaraldehyde were found after 4 weeks in saline at 37° C., indicating that slow but constant leaching of glutaraldehyde can occur in vivo. Table 1 illustrates that if two of the saline steps are replaced with incubations in glycine solution in accordance with the present invention (steps 2 and 3), glutaraldehyde concentration drops substantially. After prolonged incubation in saline at 37° C., very low amounts of glutaraldehyde moieties were found in the glycine treated tissue, indicating that neutralization was complete and irreversible.

Example 2—Cytotoxicity

Pure collagen gels were cast in tissue plates and the gels were divided into two groups: (1) neutralized—gels were fixed 15 minutes with buffered glutaraldehyde, washed and neutralized with glycine as described in example 1, and (2) control—gels were fixed 15 minutes with buffered glutaraldehyde, washed in saline. Fibroblasts were isolated from fresh bovine pericardium by the explant technique and 1500 cells per $cm^2$ were seeded on top of all gels. Cells were fed every 3 days and cell attachment and proliferation was observed at 1 hour, 2 hours, 19 hours, 4 days, 5 days and 14 days after seeding. The number of cells was evaluated by counting the entire surface of the gels. Table 2 illustrates the results of these evaluations.

TABLE 2

Cell Numbers on Collagen Gels (cells per $cm^2$ ± SD, n = 10)

| Time After Seeding | Control | Neutralized |
|---|---|---|
| 1 hour | 1200 ± 120 | 1250 ± 125 |
| 2 hours | 1100 ± 100 | 1100 ± 110 |
| 19 hours | 1000 ± 85 | 1000 ± 98 |
| 4 days | 840 ± 77 | 1800 ± 120 |
| 5 days | 700 ± 64 | 2200 ± 145 |
| 14 days | 480 ± 58 | 2400 ± 150 |

Cells that were seeded onto gels which were glutaraldehyde fixed and washed without glycine (control group), attached to the gels but did not spread and remained rounded even after 14 days of culture. Cells attached and spread rapidly onto the glycine neutralized gels and proliferated in three-dimensions populating the gels with increasing numbers. These results indicate that glutaraldehyde fixed collagen gels or tissues, are highly cytotoxic to living cells unless the residual glutaraldehyde moieties are quenched or neutralized with glycine. This is important when repopulation of fixed tissue with host fibroblasts or endothelium is taken into consideration. Also, because of the short fixation time and the rapid stabilization procedure it is possible that a certain proportion of the cells that reside initially in the connective tissue "core" may escape the cytotoxic effect of glutaraldehyde and provide a metabolic entity that will increase the in vivo durability of crosslinked biomaterials. Moreover, implantation of aldehyde treated but not neutralized tissues in close vicinity to host living tissues (heart muscle, valvular fibrous rings, arterial wall and the like) may induce local proinflammatory reactions due to the slow release of cytotoxic and irritant aldehyde molocules.

Example 3—Crosslinking

Pericardial tissue was fixed at room temperature for 15 minutes and neutralized as described in example 1 (neutralized) and hydrothermal shrinkage temperature was compared with same tissue fixed for 14 days in the same glutaraldehyde solution (control), without neutralization. Hydrothermal shrinkage temperature is an indicator of the degree of crosslinking of collagenous biological tissues; the higher the temperature the more crosslinked the tissue. The experiment setup is comprised of a 1 cm by 1.5 cm tissue samples mounted between the two clamps of a LVDT (linear vertical displacement transducer) and immersed in water. The water temperature was raised by 1° C./min. until shrinkage of tissue is detected by the LVDT. Sensitivity of the technique is 0.25° C.

Another test that provides information on the mechanical strength of tissue samples is the "suture holding power" which designates the resistance of a tissue sample towards a force applied to a suture line mounted on the tissue. For this test, 1 cm by 1.5 cm tissue samples from both groups were mounted on one side with a clamp (connected to the LVDT) and the opposite side was fixed to a non-moving second clamp by a single suture (Prolene 3/O). A continuous measurable force was applied to the suture-holding clamp and the point of tissue rupture was recorded and expressed as $N/cm^2$ (tissue cross section, i.e., thickness by width).

Samples from the two groups were also analyzed for their resistance to collagenase digestion as follows: equal amounts of tissue were incubated overnight in 0.1 U of bacterial collagenase (in calcium containing buffer), at 37° C. and the amount of released aminoacids was assayed with a ninhydrin technique. Sensitivity of the technique is 5 ug aminoacids/ml. Resistance to collagenase is expressed as a percentage of the total digestion sample (fresh, unfixed tissue incubated with collagenase under similar conditions).

Table 3 illustrates the results of these three tests for crosslinking and compares the results to fresh pericardium.

TABLE 3

Crosslinking of Pericardium

| Samples | ST | SHP | RC |
|---|---|---|---|
| Fresh | 66.4 ± 1.3 | 23 ± 3 | 5.1 ± 1 |
| Neutralized | 80.2 ± 1.4 | 41 ± 4 | 92 ± 4 |
| Control* | 85.1 ± 1.3 | 44 ± 6 | 95 ± 3 |

*14 days fixed tissue
ST—shrinkage temperature, ° C. ± SD
SHP—suture holding power, $N/cm^2$ ± SD
RC—resistance to collagenase, % of total ± SD
(n = 10 or all tests)

By comparison with fresh tissue (unfixed), pericardium treated with the rapid fixation and neutralization protocol (neutralized) was characterized by an increased number of crosslinks revealed by a significant raise in shrinkage temperature (about 14° C.), a dramatic change in resistance to collagenase (18-fold) and two-fold increase in the suture holding power. By comparison to the control group pericardium, the neutralized tissue has a slightly lower shrinkage temperature but otherwise shares similar suture holding power and resistance to collagenase indicating that the short fixation protocol introduced a sufficient number of crosslinks and did not significantly modify the mechanical strength and the biochemical characteristics of the tissue.

Example 4—Biocompatibility

Neutralized group bovine pericardial tissue (fixed with the rapid glutaraldehyde/glycine protocol) was implanted subcutaneously in mature Wistar rats (200 gr.) and explanted after 14 weeks. Control tissue (fixed for 14 days and not neutralized) was implanted for comparison. After explantation, samples were analyzed by histology. In control samples, moderate to severe leukocytic infiltration was noted alongside with a moderate fibrotic proinflammatory adjacent host tissue reaction. In neutralized tissue samples, cell infiltration and host tissue reaction was minimal. These results suggest that glutaraldehyde fixed tissues are rendered biocompatible after glycine neutralization.

Example 5—Calcification

Neutralized group bovine pericardial tissue (fixed with the rapid glutaraldehyde/glycine protocol) was implanted subcutaneously in weaning Wistar rats (60 gr.) and explanted after 8 weeks. Control tissue (fixed for 14 days and not neutralized) was implanted for comparison. After explantation, tissues were analyzed for calcium content by atomic absorption spectrophotometry on acid hydrolyzed samples. (This experiment model for accelerated calcification has been utilized for studies on bioprosthetic calcification. Tissues calcified in this experiment share similar characteristics with the clinical aspects. It is believed that the accelerated calcium deposition occurs due to the shorter period of time during which the rats reach maturity and stop depositing calcium. The "compressed" life span of the animals facilitates calcification studies but can not always be extrapolated to the human clinical situations.)

By comparison with the control group pericardium, which accumulated high amounts of calcium (112±20 ug Ca/mg dry weight, mean±SD for n=12) the neutralized tissue exhibited a reduced tendency to calcification (23±8 ug Ca/mg dry weight, mean±SD for n=12). These results suggest that lower incorporation of glutaraldehyde into connective tissues, corroborated with the effective neutralization of residual aldehyde groups, can reduce the long term calcification of bioprostheses.

Although the present invention has been described with reference to preferred embodiments, workers skilled in the art will recognize that changes may be made in form and detail without departing from the spirit and scope of the invention.

What is claimed is:

1. A method for rapid fixation and neutralization of autologous biological tissue that renders the tissue suitable for animal and human implantation comprising:
   treating a animal or human tissue with an effective amount of glutaraldehyde which promotes tissue crosslinking; and
   treating the animal or human tissue with an unbranched alpha amino acid solution.

2. The method of claim 1 wherein the rapid fixation and neutralization of autologous biological tissues is performed onto connective tissues selected from the group consisting of pericardium, cardiac valves, arterial and venous walls, fascia lata, tendons, skin, trachea and medical devices that incorporate rapidly fixed and neutralized tissue.

3. The method of claim 1 wherein the unbranched alpha amino acid is of such a concentration as to neutralize residual glutaraldehyde.

4. The method of claim 1 wherein the unbranched alpha amino acid solution has a pH of about 7.4.

5. The method of claim 1 wherein the treating of the animal or human tissue with the unbranched alpha amino acid solution is for a period of about 8 to about 15 minutes.

6. A method for the rapid chemical treatment of autologous connective tissues which enhances biocompatibility by reducing cytotoxicity, immunogenicity and calcification without impairing the mechanical properties of the tissue comprising:
   exposing the autologous connective tissue to a dialdehyde fixative for about 8 to about 15 minutes; and
   rapidly neutralizing excess aldehyde on the tissue with an unbranched alpha aminoacid solution.

7. The method of claim 6 wherein the dialdehyde fixative contains an effective amount of dialdehyde to promote tissue crosslinking.

8. The method of claim 6 wherein the aminoacid solution is of such a concentration as to neutralize residual dialdehyde fixative.

9. A method for rapid fixation and neutralization of autologous biological tissue that renders the tissue suitable for animal and human implantation comprising:
   treating a animal or human tissue with an effective amount of glutaraldehyde which promotes tissue crosslinking for a period of about 8 to about 15 minutes; and
   treating the animal or human tissue with an unbranched alpha aminoacid solution having a pH of about 7.4 for a period of about 8 to about 30 minutes.

10. The method of claim 9 wherein the effective amount of glutaraldehyde is about 0.2 to 0.7% in a buffered solution.

11. The method of claim 9 wherein the rapid fixation and neutralization of autologous biological tissues is performed onto connective tissues selected from the group consisting of pericardium, cardiac valves, arterial and venous walls, fascia lata, tendons, skin, trachea and medical devices that incorporate rapidly fixed and neutralized tissue.

12. A method for the rapid chemical treatment of autologous connective tissues which enhances biocompatibility by reducing cytotoxicity, immunogenicity and calcification without impairing the mechanical properties of the autologous connective tissue comprising:
   exposing the autologous connective tissue to a dialdehyde fixative; and
   neutralizing excess aldehyde on the autologous connective tissue with an unbranched alpha aminoacid solution for about 8 to about 30 minutes.

13. The method of claim 12 wherein the neutralizing of excess aldehyde on the autologos connective tissue is for a first period of about 8 to about 15 minutes and a second period of about 8 to about 15 minutes.

14. The method of claim 12 wherein the aminoacid solution has a pH of about 7.4.

15. The method of claim 12 wherein the exposing of the autologous connective tissue to the dialdehyde fixative is for a period of about 8 to about 15 minutes.

16. The method of claim 12 wherein the dialdehyde fixative contains an effective amount of dialdehyde to promote tissue crosslinking.

* * * * *